United States Patent [19]

Preikschat

[11] 4,181,881
[45] Jan. 1, 1980

[54] ELECTRICAL IMPEDANCE MEASURING APPARATUS FOR PROVIDING SEPARATE MEASUREMENTS OF THE CONDUCTIVITY AND DIELECTRIC COEFFICIENT OF VARIOUS MATERIALS

[76] Inventor: Fritz K. Preikschat, 16020 Lake Hills Blvd., Bellevue, Wash. 98008

[21] Appl. No.: 905,794

[22] Filed: May 15, 1978

[51] Int. Cl.² ............................................. G01R 27/00
[52] U.S. Cl. .............................. 324/57 R; 324/61 R; 324/DIG. 1
[58] Field of Search ................ 324/57 R, 61 R, 62 R, 324/DIG. 1

[56] References Cited

U.S. PATENT DOCUMENTS

| | | | |
|---|---|---|---|
| 3,584,297 | 6/1971 | Koski | 324/57 R |
| 3,746,975 | 7/1973 | Maltby | 324/61 R X |
| 3,778,707 | 12/1973 | Vogel | 324/61 R |
| 3,873,927 | 3/1975 | Overall | 324/61 R X |

*Primary Examiner*—Stanley T. Krawczewicz
*Attorney, Agent, or Firm*—Christensen, O'Connor, Johnson & Kindness

[57] ABSTRACT

An oscillator provides an output signal, of frequency $f_0$, whose phase is shifted by substantially 45° to obtain a test signal which is coupled by a first cable to a bridge circuit located in proximity to a sample box and interconnected with an active, center electrode of that sample box. In response to the test signal, the bridge circuit provides a bridge output signal whose frequency is identical to that of the test signal and whose phase, relative to that of the test signal, and whose amplitude are related to the electrical admittance of particulate material within the sample box. The oscillator output signal is also applied to a phase-shifting network which provides first, second, third and fourth signals respectively in-phase, 90° out-of-phase, 180° out-of-phase, and 270° out-of-phase with the test signal. A switching circuit couples the first, second, third and fourth signals to its output in a predetermined sequence and at a frequency of $f_a$, wherein $f_0$ is much greater than $f_a$, to develop a reference signal which is coupled by a second cable to a first input of a double-balanced mixer located in proximity to the bridge circuit. The bridge output signal is applied to a second input of the double-balanced mixer, whereby a time-multiplexed mixer output signal is provided which has four successive DC levels proportional to positive and negative values of the conductance and susceptance components of the bridge output signal. The mixer output signal is coupled via the second cable and temperature and bulk density compensation circuits to first, second, third and fourth sample and hold circuits. The first and third sample and hold circuits store successive DC levels of the mixer output signal corresponding to positive and negative values of the conductance component, and the second and fourth sample and hold circuits store successive DC levels of the mixer output signal corresponding to positive and negative values of the susceptance component. A first operational amplifer takes the absolute difference of the stored DC levels in the first and third sample and hold circuits to provide a first output signal proportional to the conductivity of the particulate material, and a second operational amplifier takes the absolute difference of the DC level stored in the second and fourth sample and hold circuits to provide a second output signal proportional to the dielectric coefficient of the particulate material.

23 Claims, 5 Drawing Figures

ELECTRICAL IMPEDANCE MEASURING APPARATUS FOR PROVIDING SEPARATE MEASUREMENTS OF THE CONDUCTIVITY AND DIELECTRIC COEFFICIENT OF VARIOUS MATERIALS

FIELD OF THE INVENTION

This invention generally relates to electrical impedance measuring apparatus, and more particularly, to improvements in such apparatus which allow the apparatus to provide accurate, precise and separate measurements of the conductivity and dielectric coefficient of various materials.

BACKGROUND OF THE INVENTION

Apparatus is known to the prior art for measuring the electrical impedance of various materials, such as wood chips, grain, hogged fuel, sawdust, coal and various ore concentrates. The measurements may be made on a continuous basis, in which the material is continuously flowing past an electrode forming part of the apparatus, or on a sampling basis, in which a sample of the material is placed in a container including or forming part of the electrode.

An electrical impedance measuring apparatus particularly suited for sampling measurements is disclosed in U.S. Pat. No. 3,781,671, issued Dec. 25, 1973 to Fritz K. Preikschat, and entitled AN IMPEDANCE MEASURING BRIDGE CIRCUIT; U.S. Pat. No. 3,824,461, issued July 16, 1974 to Fritz K. Preikschat, and entitled ELECTRICAL IMPEDANCE MEASURING APPARATUS; and U.S. Pat. No. 3,992,665, issued Nov. 16, 1976 to Fritz K. Preikschat, and entitled ELECTRICAL IMPEDANCE MEASURING APPARATUS. Each of the foregoing patents is expressly incorporated by reference herein.

As disclosed in the aforementioned patents, a sample box for particulate material includes a grounded electrode portion which is shaped as a box having a substantially rectangular cross section. An active center electrode, typically comprising a metallic plate, is disposed in the interior of the sample box defined by the grounded electrode portion and in parallel, spaced relationship to the side walls thereof so that a uniform electrical field may be created within the sample box. The sample box has an inlet and an outlet which, together with the grounded electrode portion and the active center electrode, define a constant volume into which a sample of particulate material may be placed and retained for measurement.

A signal generator provides a test signal, having a certain frequency typically in the megacycle range, to a bridge circuit which in turn is interconnected with the active center electrode of the sample box and with ground potential. In operation, the bridge circuit provides a high frequency electrical signal to the active center electrode which thereby creates a high frequency electrical field in the interior of the sample box and therefore in the sample contained therein. The electrical impedance of the sample causes an imbalance in the bridge circuit so that the bridge circuit provides an electrical output signal whose phase, relative to the phase of the test signal from the signal generator, and whose amplitude are related to the electrical admittance, or reciprocal impedance, of the sample.

After compensation for temperature and bulk density variations of the sample, if needed, the bridge output signal is then supplied to a controllable rectifier which is also supplied with a reference signal whose frequency is identical to that of the test signal and whose phase has a predetermined relationship to that of the test signal. If the phase of the reference signal is in-phase with that of the test signal, then the controllable rectifier operates to provide a DC signal related to the conductance, or conductivity, component of the measured electrical admittance. If the phase of the reference signal is 90° out-of-phase with that of the test signal, then the controllable rectifier operates to provide a DC signal related to the susceptance, or dielectric coefficient, component of the measured electrical admittance.

In the measurement of the electrical impedance of certain particulate materials, such as wood chips, very low dielectric coefficients, resulting in capacitances in the range of 60 to 400 picofarads, are often encountered, as are very high conductivities in the order of 20,000 micromhos (or, a resistance of 50 ohms). In order to very accurately and precisely measure such values of dielectric coefficient and conductivity, the test and reference signals provided in the electrical impedance measuring apparatus of the prior art must have a very high phase stability and should be relatively free of harmonics. Further, the phase relationship of the reference signal to the test signal, and to the bridge output signal, must be precisely controllable in order to insure reliable separation and determination of the conductance and susceptance components of the bridge output signal. It has proven to be very difficult, using an electrical impedance measuring apparatus as disclosed in the aforementioned patents, to obtain and maintain such phase stability, low harmonic content, and phase relationship control, so that reliable measurement of dielectric coefficient and conductivity cannot be insured for values thereof in the ranges previously discussed.

It is therefore an object of this invention to provide an electrical impedance measuring apparatus which is capable of more accurately and precisely measuring the conductivity and dielectric coefficient of various particulate materials than is the electrical impedance measuring apparatus of the prior art.

It is further object of this invention to provide such an improved electrical impedance measuring apparatus which provides separate measurements of conductivity and dielectric coefficient.

SUMMARY OF THE INVENTION

Briefly, these objects and others that will be realized by one skilled in the art, are achieved by an improved apparatus for use in providing separate measurements of the conductivity and dielectric coefficient of various materials. The apparatus comprises first means for providing a test signal having a predetermined frequency $f_0$. A second means is responsive to the test signal for providing an output signal whose frequency is identical to that of the test signal and whose phase, relative to that of the test signal, and whose amplitude are related to the measured electrical admittance of the particulate material. A third means provides a reference signal whose frequency is identical to that of the test signal, the third means being adapted to shift the phase of the reference signal at a frequency $f_\alpha$, where $f_0$ is much greater than $f_\alpha$, so that the reference signal successively has a substantially in-phase and a substantially 90° out-of-phase relationship with the test signal. A fourth means mixes the output signal from the second means and the reference signal to provide an output signal whose amplitude is successively related to the conductivity and to the dielectric coefficient of the material.

A preferred embodiment of the apparatus comprises first means for providing a test signal having the frequency $f_0$, and a second means for providing a reference signal whose frequency is identical to that of the test signal, the second means being adapted to successively shift the phase of the reference signal at the frequency $f_\alpha$ so that the reference signal is substantially in-phase, 90° out-of-phase, 180° and out-of-phase, and 270° out-of-phase with the test signal. An electrode is adapted to be located in the vicinity of the material to be measured, and a bridge circuit is adapted to be located in proximity to the electrode and has first and second inputs and an output. A third means interconnects the electrode with the second input of the bridge circuit, and a fourth means couples the test signal to the first input of the bridge circuit, whereby the bridge circuit provides a bridge output signal on its output whose frequency is identical to that of the test signal and whose phase, relative to that of the test signal, and whose amplitude are related to the electrical admittance of the material in the vicinity of the electrode. A mixer is provided which is adapted to be located in proximity to the electrode, the mixer having first and second inputs and an output. Fifth means couples the bridge output signal to the second input of the mixer, and sixth means couples the reference signal to the first input of the mixer, whereby the mixer provides a time-multiplexed mixer output signal on its output which has successive first, second, third and fourth DC levels which are respectively proportional to a positive conductance component, to a positive susceptance component, to a negative conductance component, and to a negative susceptance component, of the bridge output signal.

Means may also be provided for storing the first, second, third and fourth DC levels. The absolute difference between the stored first and third DC levels is taken to provide a first output signal proportional to the conductivity of the material, and the absolute difference between the stored second and fourth DC levels is taken to provide a second output signal proportional to the dielectric coefficient of the material.

BRIEF DESCRIPTION OF THE DRAWINGS

The invention can best be understood by reference to the following portion of the specification, taken in conjunction with the accompanying drawings, in which.

DESCRIPTION OF THE PREFERRED EMBODIMENT

Figure 1:
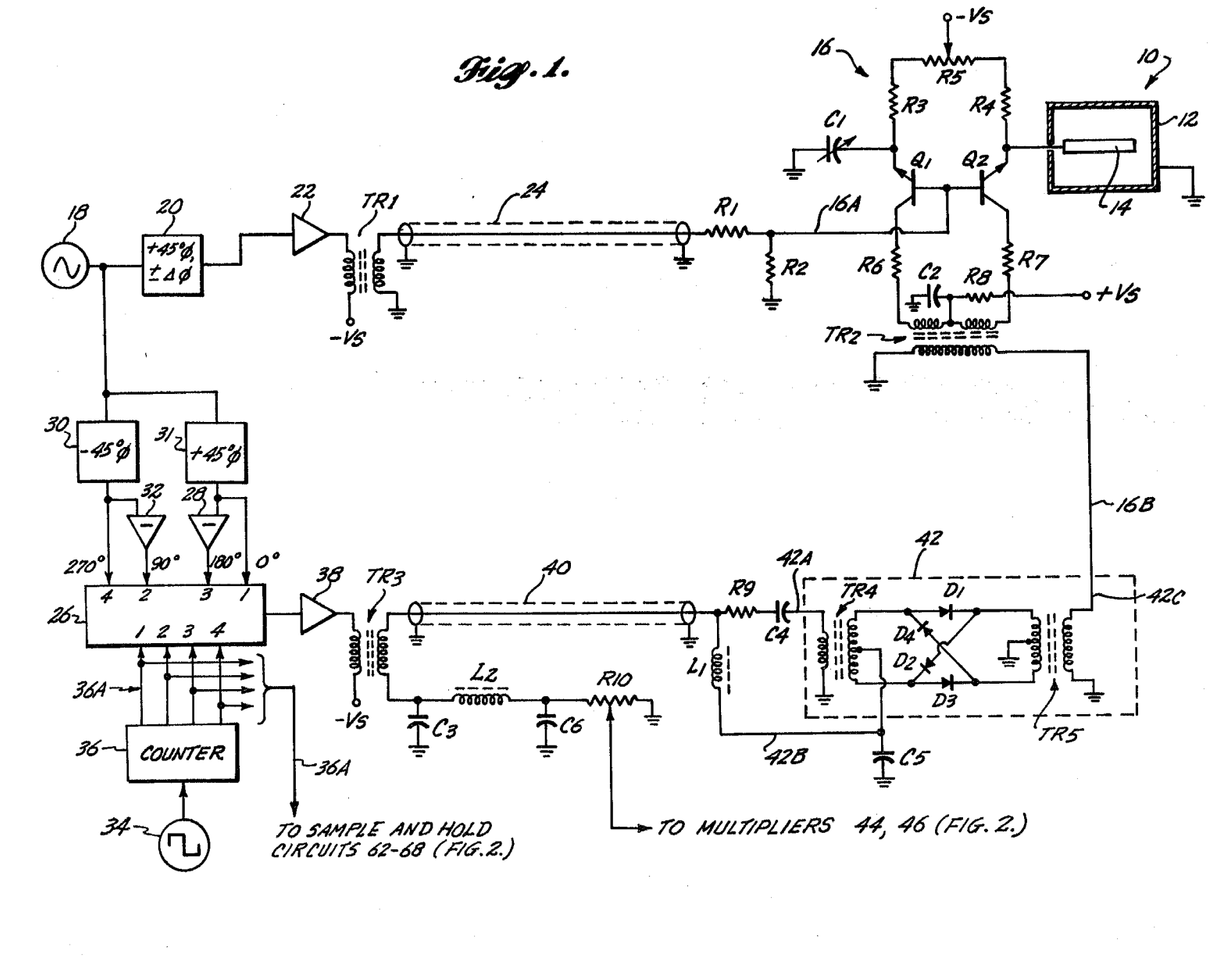
FIG. 1 is a combined schematic and block diagram of a first portion of a preferred embodiment of the improved electrical impedance measuring apparatus of the present invention including an improved bridge circuit providing an output signal whose phase and amplitude are related to the measured electrical admittance of particulate material, a double-balanced mixer for demodulating the bridge output signal and for providing a time-multiplexed mixer output signal, and a source of test and reference signals for operation of the bridge circuit and the double-balanced mixer.

With reference now to FIG. 1, the invention will be described with reference to an electrical impedance measuring apparatus of the type adapted to make measurements on a sample of particulate material, although it is to be clearly understood that the present invention can also be embodied in apparatus which measures the electrical impedance of other types of material on a continuous or on a sampling basis.

A sample box 10, which may be of a type more completely described in the aforementioned U.S. Pat. Nos. 3,781,671, 3,824,461 and 3,992,665, is shown in plan view and includes a grounded electrode portion 12 which is shaped as a box having a substantially rectangular cross section. An active center electrode 14, comprising a metallic plate, is disposed in the interior of the sample box 10 defined by grounded electrode portion 12 and in parallel, spaced relationship to the side walls thereof so that a substantially uniform electrical field may be created within the sample box 10. Sample box 10 has an inlet and an outlet, not illustrated, which together with the grounded electrode portion 12 and the active center electrode 14 define a constant volume within the sample box 10 into which a sample of particulate material is placed and retained for measurement.

The active center electrode 12 is interconnected with, and forms part of, a bridge circuit 16, to be described in more detail hereinafter, which is adapted to be imbalanced by and in relation to the electrical impedance of the particulate material contained within the sample box 10. The bridge circuit 16 receives, on its input 16A, a high frequency test signal, and provides, on its output 16B, an output signal whose frequency is identical to that of the test signal and whose phase, relative to the phase of the test signal, and whose amplitude are related to the electrical admittance, or reciprocal impedance, of the particulate material within the sample box 10.

The test signal appearing on input 16A is obtained in the following manner. An oscillator 18 provides an output signal having a sinusoidal waveform and a frequency $f_0$, preferably in the megacycle range. Preferably, oscillator 18 is crystal controlled to have a high degree of frequency and phase stability and provides an output signal which is relatively free of harmonics. The output signal from oscillator 18 is applied to the input of a phase shift circuit 20 which provides a corresponding output signal whose phase is advanced 45° from that of the output signal from oscillator 18. Phase shift circuit 20 is also capable of being adjusted to vary the phase of its output signal by an amount $\Delta\phi$ for purposes to be hereinafter described. The output signal from phase shift circuit 20 is applied to the input of an amplifier 22 which provides a corresponding output signal whose amplitude is carefully regulated, preferably to better than ±1%, since accurate measurement of the value of the conductivity and dielectric coefficient of the particulate material within sample box 10 is dependent on the amplitude stability of the test signal suppled to the bridge circuit 16.

The output signal from amplifier 22, which is the test signal, is applied to one side of the primary winding of a transformer $TR_1$ whose other side is coupled to a negative supply voltage $-V_s$. The test signal appears in the secondary winding of transformer $TR_1$ (which is connected to ground potential) and is coupled to a shielded cable 24 which extends to the bridge circuit 16 (which preferably is located in proximity to the sample box 10). To minimize noise pick-up, the shield of cable 24 is connected to ground potential at its ends adjacent transformer $TR_1$ and bridge circuit 16.

In a typical installation, the bridge circuit 16 may be located at a considerable distance (e.g., 100 feet) from oscillator 18 and its associated components. The length of cable 24 is therefore not negligible with respect to the wavelength of the test signal so that the cable 24 must be terminated at each end with an impedance substantially equal to the characteristic impedance of the cable to prevent standing waves from being produced which would cause phase and amplitude shifts in the test signal. At the location of oscillator 18 and its associated components, the cable impedance is matched by that of transformer $TR_1$. At the location of bridge circuit 16 and its associated components, the cable 24 is connected to the input 16A of the bridge circuit 16 via a resistor $R_1$, and a resistor $R_2$ couples the input 16A to ground potential. Within bridge circuit 16, the input 16A is connected to the bases of transistors $Q_1$ and $Q_2$. The impedance therefore presented to cable 24 at the location of the bridge circuit 16 comprises the base impedance of transistors $Q_1$ and $Q_2$ and the impedance of the resistors $R_1$, $R_2$, with the values of resistors $R_1$ and $R_2$ being chosen to match the cable impedance.

The emitter of transistor $Q_1$ is coupled by a resistor $R_3$ to one side of a potentiometer $R_5$, and the emitter of transistor $Q_2$ is coupled by a resistor $R_4$ to the other side of potentiometer $R_5$. The tap of potentiometer $R_5$ is connected to the negative supply voltage $-V_s$. An adjustable capacitor $C_1$ is connected from the common junction of resistor $R_3$ and the emitter of transistor $Q_1$ to ground potential, and the active center electrode 14 is connected to the common junction of resistor $R_4$ and the emitter of transistor $Q_2$. A resistor $R_6$ couples the collector of transistor $Q_1$ to one side of the primary winding of a transformer $TR_2$, and a resistor $R_7$ couples from the collector of transistor $Q_2$ to the other side of the primary winding of transformer $TR_2$. The primary winding of transformer $TR_2$ is split into first and second substantially symmetrical portions connected in series opposition and having a common center tap. Capacitor $C_2$ is connected from this center tap to ground potential, and resistor $R_8$ is connected from the center tap to a positive supply voltage $+V_s$. Transformer $TR_2$ is also provided with a single secondary winding whose one side is connected to ground potential and whose other side is connected to the output 16B of the bridge circuit 16 upon which the bridge output signal appears.

Since the impedance to be measured has very low values with respect to the characteristic impedance of the cable 24 (e.g., 50 ohms), transistors $Q_1$ and $Q_2$ are chosen to have a relatively high base impedance and a relatively low emitter impedance to therefore isolate the remainder of the bridge circuit 16 from the portion of the apparatus supplying the test signal including cable 24.

Resistor $R_8$ functions to develop an operating voltage for the collectors of transistors $Q_1$ and $Q_2$, and capacitor $C_2$ functions to maintain this operating voltage while yet providing a path to ground potential for alternating current signals present in the first and second portions of the primary winding of transformer $TR_2$.

The test signal is applied through transistor $Q_2$ to the active center electrode 14 so as to result the production of a high frequency electrical field within the sample box 10. As can be appreciated, the impedance connected to the emitter of each of the transistors $Q_1$, $Q_2$ determines the amplitude and phase of the emitter current of each transistor, and therefore the amplitude and phase of the collector current of each transistor. Since the collectors of transistors $Q_1$ and $Q_2$ are coupled to opposite sides of the primary winding of transformer $TR_2$, and since the first and second portions of that primary winding are substantially symmetrical and connected in series opposition, equal collector currents of transistors $Q_1$, $Q_2$ will produce equal, opposing magnetic fluxes in transformer $TR_2$ so that no bridge output signal is produced in the secondary winding thereof. When the sample box 10 is empty, capacitor $C_1$ and potentiometer $R_5$ are adjusted so that the bridge circuit 16 is balanced, that is, the collector currents of transistors $Q_1$, $Q_2$ are equal. When particulate material is placed in the sample box 10, the bridge circuit 16 is imbalanced to cause the production of a bridge output signal on output 16B whose amplitude and phase are related to the electrical admittance of the particulate material within sample box 10 and whose frequency $f_0$ is identical to that of the test signal.

In order to reliably separate the conductance and susceptance components of the measured electrical admittance, which components are represented by the amplitude and phase information in the bridge output signal, the bridge output signal must be demodulated. In order to effect this demodulation, a reference signal, of a frequency $f_0$ identical to that of the test signal, and therefore to that of the bridge output signal, and of carefully controlled phase and amplitude, must be produced and supplied to the vicinity of the bridge circuit 16.

To develop the reference signal, the output signal from oscillator 18 is applied to the input of a phase shift circuit 31 which provides a corresponding output signal whose phase is advanced 45° from that of the output signal from oscillator 18. The output signal from phase shift circuit 31 is applied directly to a first signal input of a switch 26 and to a third signal input of switch 26 through an inverter 28. The output signal from oscillator 18 is also applied to the input of a phase shift circuit 30 which provides a corresponding output signal whose phase is retarded 45° from that of the output signal from oscillator 18. The output signal from phase shift circuit 30 is applied directly to a fourth signal input of switch 26 and through an inverter 32 to a second signal input of switch 26. Those skilled in the art will appreciate that the signals thus applied to the first, second, third and fourth signal inputs of switch 26 are respectively in-phase, 90° out-of-phase, 180° out-of-phase, and 270° out-of-phase, with the test signal.

An oscillator 34 provides an output signal, having a substantially square waveform and a frequency preferably in the audio frequency range, to a counter 36 which preferably comprises a divide-by-4 counter adapted to provide a sequence of four output signals on its outputs 36A thereof, each output signal having a duration equal to the period of the output signal from oscillator 34. The outputs 36A are coupled to respective first, second, third and fourth control inputs of switch 26, as a result of which switch 26 is enabled to couple to its output the signals applied to its first, second, third and fourth signal inputs in sequence. As a result, the signal appearing on the output of switch 26 has a frequency $f_0$ which is identical to that of the test signal, and a phase which is sequentially in-phase, 90° out-of-phase, 180° out-of-phase, and 270° out-of-phase, with that of the test signal, and with switching between said phases being effected at a relatively low frequency $f_\alpha$ determined by the repetition rate of the output signals from counter 36, where $f_0$ is much greater than $f_\alpha$, e.g., $f_0 \simeq 1000 f_\alpha$.

The signal appearing at the output of switch 26 is applied to the input of an amplifier 38 which provides a corresponding output signal which comprises the reference signal and which is applied to one side of the primary winding of a transformer $TR_3$ whose other side is coupled to the negative supply voltage $-V_s$. One side of the secondary winding of transformer $TR_3$ is connected to ground potential by a capacitor $C_3$, and the other side is connected to a shielded cable 40 which extends to the vicinity of the bridge circuit 16. As is the case with cable 24, the shield of cable 40 is connected to ground potential at its ends adjacent transformer $TR_3$ and the vicinity of the bridge circuit 16. To prevent the reference signal from being shifted in either amplitude or phase relative to the test signal, the cable 40 is of an identical type and length to cable 24. Further, transformer $TR_3$ is of an identical type and impedance to transformer $TR_1$.

At the vicinity of the bridge circuit 16, the cable 40 is connected to a first input 42A of a double-balanced mixer 42 by a resistor $R_9$ and a capacitor $C_4$ connected in series circuit. Within double-balanced mixer 42, the first input 42A is connected to one side of the primary winding of a transformer $TR_4$ whose other side is connected to ground potential. The secondary winding of transformer $TR_4$ has first and second, substantially symmetrical portions connected in series opposition and having a center tap which serves as an output 42B for the double-balanced mixer 42. Capacitor $C_5$ is connected from the center tap of the secondary winding of transformer $TR_4$ to ground potential, and output 42B is coupled to the cable 40 through an inductor $L_1$. The output 16B from the bridge circuit 16 is connected to a second input 42C of the double-balanced mixer 42 which in turn is connected to one side of the primary winding of a transformer $TR_5$ whose other side is connected to ground potential. The secondary winding of transformer $TR_5$ includes first and second, symmetrical portions connected in series opposition and having a center tap connected to ground potential. Interconnecting the secondary windings of transformers $TR_4$ and $TR_5$ is a ring circuit of diodes $D_1$, $D_2$, $D_3$ and $D_4$. As can be seen, this ring circuit is such that all of the diodes $D_1$–$D_4$ are poled to conduct in the same direction around the ring.

Figure 3:
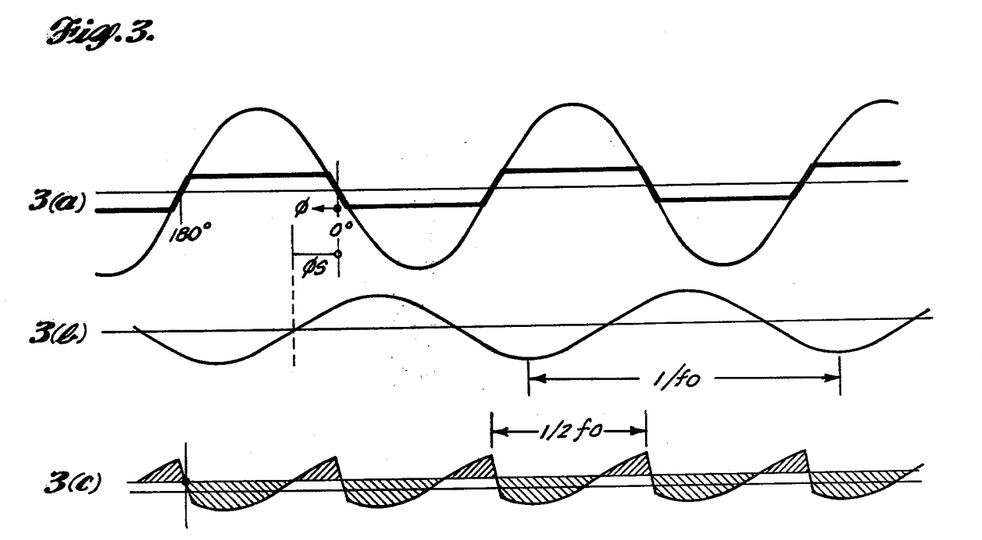
FIG. 3 is a waveform diagram illustrating the test, reference and phase-demodulated bridge output signals, for a given phase of the reference signal.

To understand the operation of the double-balanced mixer 42, let it be assumed that the reference signal has been applied to the input 42A thereof and that no output signal is being provided from the bridge circuit 16 on output 16B. Under these conditions, diodes $D_1$ and $D_2$ will provide a conducting path across the secondary windings of transformers $TR_4$ and $TR_5$ during positive half-cycles of the reference signal, and diodes $D_3$ and $D_4$ will provide a conducting path across the secondary windings of transformers $TR_4$ and $TR_5$ during negative half-cycles of the reference signal. The voltage drop across each secondary winding will be equal to the sum of the forward conduction voltages of the pair of diodes that is conducting, so that the reference signal appearing across the secondary windings is clipped as illustrated by the heavy line curve in FIG. 3(a). Since there is no input signal being provided to the second input 42C of the double-balanced mixer 42, the currents through each of the conducting diodes ($D_1$, $D_2$, or $D_3$, $D_4$) will be equal. As a result, no current will flow through the center tap of the secondary winding of transformer $TR_4$ and the mixer output signal on output 42B will be zero.

Let it now be assumed that the reference signal being applied to the double-balanced mixer 42 is in-phase with the test signal supplied to the bridge circuit 16, and that the bridge circuit 16 is providing an output signal on output 16B which has a certain amplitude and whose phase is shifted by an amount $\phi_s$ with respect to that of the test signal, and therefore of the reference signal, as illustrated in FIGS. 3(a) and 3(b). Under these conditions, and as long as the magnitude of the bridge output signal appearing across the secondary winding of transformer $TR_5$ is less than that of the clipped reference signal appearing across the secondary winding of transformer $TR_4$, unequal currents will flow in the conducting diodes ($D_1$, $D_2$, or $D_3$, $D_4$) so that there is current flow through the tap of the secondary winding of transformer $TR_4$ whose frequency is twice that of the bridge output signal, or $2f_0$, and whose average DC level is proportional to the amplitude of the component of the bridge output signal in phase with the reference signal, as illustrated in FIG. 3(c).

Figure 4:
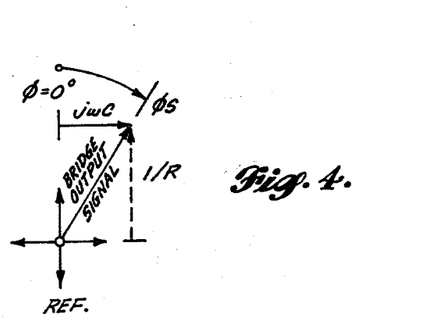
FIG. 4 is a vector diagram of the bridge output signal.
Figure 5:
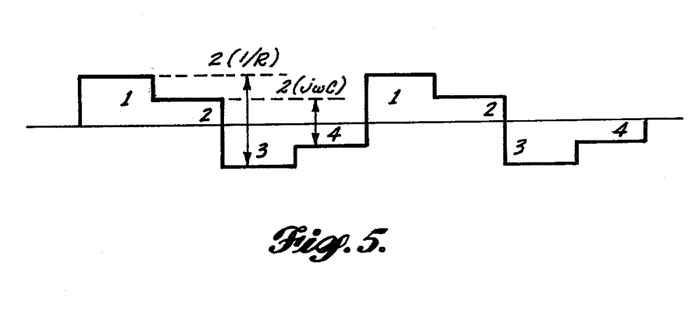
FIG. 5 is a waveform diagram illustrating the time-multiplexed mixer output signal.

As can be recalled, the phase of the reference signal, relative to that of the test signal, changes at predetermined intervals in increments of 90°. Referring to FIG. 4, the bridge output signal can be visualized as a vector having a predetermined magnitude and a phase $\phi_s$ with respect to the phase of the test signal, with the vector being capable of being resolved into a conductance component, or, that in-phase and 180° out-of-phase, with the test signal, and a susceptance component, or, that 90° out-of-phase and 270° out-of-phase with the test signal. The conductance component is proportional to the conductivity (1/R) of the measured electrical admittance and the susceptance component is proportional to the dielectric coefficient (jωC) of the measured electrical admittance. By sequentially shifting the phase of the reference signal with respect to the test signal, the output signal from the double-balanced mixer 42 is time-multiplexed at the relatively low frequency $f_\alpha$ of the output signals from counter 36 and has a DC level sequentially proportional to +(1/R), +(jωC), −(1/R) and −(jωC). The time-multiplexed mixer output signal includes equal positive and negative values of the conductivity (1/R) and the dielectric coefficient (jωC) to avoid any effect on the DC bias of the amplifiers forming succeeding parts of the apparatus of the present invention. Capacitor $C_5$ and inductor $L_1$ function to filter out the $2f_0$ component in the mixer output signal with the result that there is provided to the cable 40 a time-multiplexed signal (FIG. 5) whose frequency $f_\alpha$ is determined by that of the output signals from counter 36 and whose amplitude is sequentially proportional to the amplitude of the bridge output signal for the four sequential phase portions of the reference signal. Capacitor $C_5$ and inductor $L_1$ also function to block the reference signal from entering the double-balanced mixer 42 through its output 42B, and capacitor $C_4$ functions to block the output signal from the double-balanced mixer 42 from entering its input through input 42A. The value of resistor $R_9$ is chosen so that the double-balanced mixer 42 presents an impedance to the cable 40 which is substantially equal to that of cable 40 to prevent unwanted signal reflections in cable 40 for the purposes previously described.

The time-multiplexed output signal from the double-balanced mixer 42 is carried by the cable 40 back to the transformer $TR_3$, as a result of which the secondary winding thereof has present therein both the reference signal and the time-multiplexed mixer output signal. An inductor $L_2$ is connected from the common junction of capacitor $C_3$ and one side of the secondary winding of transformer $TR_3$ to one side of a potentiometer $R_{10}$ whose other side is connected to ground potential. A capacitor $C_6$ is connected from the common junction of inductor $L_2$ and potentiometer $R_{10}$ to ground potential. The value of capacitor $C_3$ is chosen to provide a ground for the reference signal appearing in the secondary winding of transformer $TR_3$, but is small enough so as not to have any appreciable effect on the time-multiplexed mixer output signal. Inductor $L_2$ and capacitor $C_6$ function to filter the reference signal, as a result of which there appears across potentiometer $R_{10}$ only the time-multiplexed mixer output signal.

Figure 2:
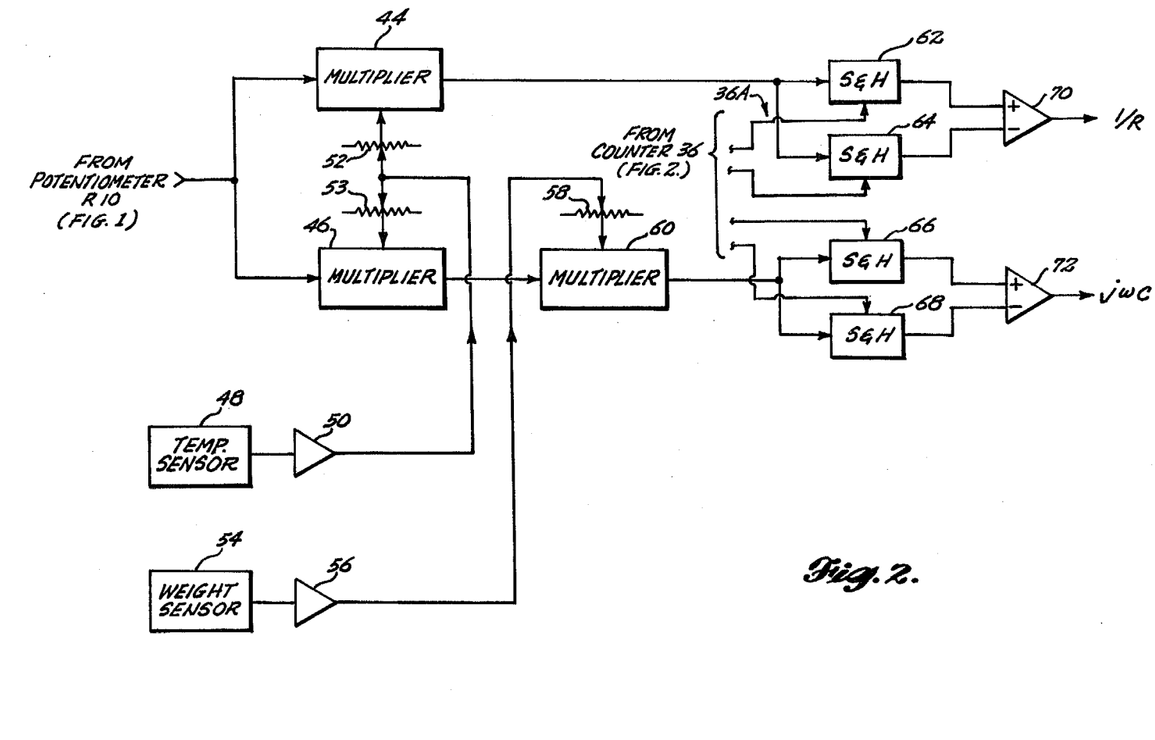
FIG. 2 is a combined schematic and block diagram of a second portion of the preferred embodiment including means for compensating the time-multiplexed output signal for temperature and bulk density variations of the particulate material and for demultiplexing the time-multiplexed output signal to separate the conductivity and dielectric coefficient components of the measured electrical admittance.

The time-multiplexed mixer output signal has its level adjusted by adjustment of the position of the tap of potentiometer $R_{10}$, and is supplied therefrom to the inputs of multipliers 44 and 46 (FIG. 2). Both the measured conductivity and the measured dielectric coefficient are subject to variation, depending on the temperature of the particulate material within sample box 10. Accordingly, a temperature sensor 48 is provided which is preferably mounted in proximity to the sample box 10 to provide an output signal which is related to the average measured temperature of the particulate material. The output signal from temperature sensor 48 is amplified in an amplifier 50 and has its level adjusted by potentiometers 52 and 53 to develop first and second temperature correction signals which are supplied to respective control inputs of multipliers 44 and 46. Preferably, multipliers 44 and 46 each comprise a four-quadrant multiplier including an operational transconductance amplifier which is operative to multiply the value of each quadrant of the time-multiplexed mixer output signal by the corresponding temperature correction signal to obtain an output signal which is compensated for temperature variations. The amount of temperature correction may be different for the measured conductivity and measured dielectric coefficient and is determined by the gain factor of amplifier 50 and the setting of potentiometers 52 and 53.

The measured dielectric coefficient is also subject to variation, depending upon the bulk density of the particulate material within sample box 10. Accordingly, a weight sensor 54 is provided which, in its preferred form, may comprise a load cell which is mounted so as to provide an output signal related to the weight of the particulate material. Since the sample box 10 has a constant volume, the output signal from weight sensor 54 is also related to bulk density. The output signal from weight sensor 54 is amplified by an amplifier 56 and has its level adjusted by a potentiometer 58 to develop a bulk density correction signal which is supplied to a control input of a multiplier 60 which is adapted to receive the output signal from multiplier 46. Preferably, multiplier 60 also comprises a four-quadrant multiplier including an operational transconductance amplifier which is operative to multiply the value of each quadrant of the time-multiplexed mixer output signal, as already adjusted by multiplier 46, by the bulk density correction signal. The amount of bulk density correction is determined by the gain factor of amplifier 56 and the setting of potentiometer 58.

The output of multiplier 44 is connected to respective signal inputs of respective sample and hold circuits 62, 64, and the output of multiplier 60 is connected to respective signal inputs of sample and hold circuits 66 and 68. Each of the sample and hold circuits 62, 64, 66 and 68 is also provided with one of the output signals appearing on outputs 36A from counter 36. For example, the output signal from outputs 36A supplied to sample and hold circuit 62 is coincident with the first phase position of the reference signal, and therefore with the $+(1/R)$ component of the time-multiplexed mixer output signal, and the output signals from outputs 36A respectively supplied to sample and hold circuits 64, 66, and 68 are coincident with the third, second, and fourth phase positions of the reference signal, and therefore with the $-(1/R)$, $+(j\omega C)$, and $-(j\omega C)$ components of the time-multiplexed mixer output signal. The output of sample hold circuit 62 is connected to the noninverting input of an operational amplifier 70, and the output of sample and hold circuit 64 is connected to the inverting input of operational amplifier 70. The output of sample and hold circuit 66 is connected to the noninverting input of an operational amplifier 72, and the output of sample and hold circuit 68 is connected to the inverting input of operational amplifier 72.

In operation, sample and hold circuits 62 and 64 are respectively controlled to store therein the $+(1/R)$ and $-(1/R)$ components of the time-multiplexed mixer output signal and to provide corresponding outputs to operational amplifier 70 whose output signal is proportional to the absolute difference between those components and therefore to the conductivity $(1/R)$ of the measured electrical admittance. Similarly, sample and hold circuits 66 and 68 are respectively controlled to store the $+(j\omega C)$ and $-(j\omega C)$ components of the time-multiplexed mixer output signal to provide corresponding outputs to operational amplifier 72 whose output signal is proportional to the absolute difference between those components and therefore to the dielectric coefficient $(j\omega C)$ of the measured electrical admittance.

To calibrate the apparatus of the present invention, the bridge circuit 16 is balanced with no sample within the sample box 10 as previously described. Then, a test box, not illustrated, and including a switch and a number of impedances of known value and type, is interconnected between the active center electrode 12 and the grounded electrode portion 14 of the sample box 10. The switch within the test box is actuated to successively connect each of the impedances therein across the sample box 10. Since phase shifts may occur in the apparatus despite the precautions that have already been described, a purely resistive impedance and a purely reactive impedance in the text box successively are connected across the sample box 10 and the phase of the test signal is adjusted (through adjustment of phase shift circuit 20 through an amount $\Delta\phi$) so that the bridge output signal provided to the second input 42C of multiplexer 42 is successively in-phase and 90° out-of-phase with the first phase position of the reference signal supplied to the first input 42A of multiplexer 42. After this phase adjustment has been made, an amplitude adjustment is made, preferably using potentiometer $R_{10}$, so that the conductivity (1/R) output signal from operational amplifier 70 is proportional to the known conductivity of one of the impedances in the test box, and so that the dielectric coefficient ($j\omega C$) output signal from operational amplifier 72 is proportional to the known dielectric coefficient of one of the impedances in the test box. Calibrating adjustments are also made, as previously described, for temperature and bulk density compensation through adjustment of potentiometers 52, 53 and 58.

While the invention has been described with reference to a preferred embodiment, it is to be clearly understood by those skilled in the art that the invention is not limited thereto, and that the scope of the invention is to be interpreted only in accordance with the appended claims.

The embodiments of the invention in which an exclusive property or privilege is claimed are defined as follows:

1. An improved apparatus for use in providing separate measurements of the conductivity and dielectric coefficient of a material, said apparatus comprising:
    (a) first means for providing a test signal having a predetermined frequency $f_0$;
    (b) second means responsive to said test signal for providing an output signal whose frequency is identical to that of said test signal and whose phase, relative to that of said test signal, and whose amplitude are related to the measured electrical admittance of said material;
    (c) third means for providing a reference signal whose frequency is identical to that of said test signal, said third means being adapted to shift the phase of said reference signal at a predetermined frequency $f_\alpha$, where $f_0$ is much greater than $f_\alpha$, so that said reference signal successively has a substantially in-phase and a substantially 90° out-of-phase relationship with said test signal; and
    (d) fourth means for mixing said output signal from said second means and said reference signal to provide an output signal which is successively related to the conductivity and to the dielectric coefficient of said material.

2. An apparatus as recited in claim 1, further comprising an oscillator for providing an oscillator output signal having a predetermined frequency, and wherein said first and said third means are each responsive to said output signal from said oscillator to respectively provide said test and said reference signals.

3. An apparatus as recited in claim 2, wherein said predetermined frequency of said oscillator is $f_0$; wherein said first means includes means responsive to said output signal from said oscillator for providing said test signal which has a predetermined phase relationship with said output signal from said oscillator; and, wherein said third means includes: means responsive to said output signal from said oscillator for providing a first signal which has a predetermined phase relationship with said output signal from said oscillator that is substantially identical to that of said test signal; means responsive to said output signal from said oscillator for providing a second signal whose phase is shifted substantially 90° with respect to that of said first signal; switching means having first and second signal inputs and a signal output, said switching means being operative when in a first position to couple said first signal input to said signal output and when in a second position to couple said second signal input to said signal output; means applying said first signal to said first signal input and said second signal to said second signal input; and, means for causing said switching means to successively switch between said first and said second positions at said frequency $f_\alpha$ to thereby provide said reference signal at said signal output of said switching means.

4. An apparatus as recited in claim 1, wherein said third means is adapted to successively shift the phase of said reference signal with respect to that of said test signal at said frequency $f_\alpha$ so that said reference signal is substantially in-phase, 90° out-of-phase, 180° out-of-phase, and 270° out-of-phase with said test signal, whereby the amplitude of said output signal from said fourth means sucessively has a positive value proportional to a conductance component of said measured electrical admittance, a positive value proportional to a susceptance component of said measured electrical admittance, a negative value proportional to said conductance component, and a negative value proportional to said susceptance component.

5. An apparatus as recited in claim 4, further comprising an oscillator for providing an output signal having a predetermined frequency, and wherein said first and said third means are each responsive to said output signal from said oscillator to respectively provide said test and said reference signals.

6. An apparatus as recited in claim 5, wherein said predetermined frequency of said oscillator is $f_0$; wherein said first means includes means responsive to said output signal from said oscillator for providing said test signal which has a predetermined phase relationship with said output signal from said oscillator; and, wherein said third means includes: means responsive to said output signal from said oscillator for providing a first signal which has a predetermined phase relationship with said oscillator output signal that is substantially identical to that of said test signal; means responsive to said output signal from said oscillator for providing a fourth signal whose phase is shifted substantially 270° with respect to that of said first signal; means for inverting said first signal to obtain a third signal whose phase is shifted substantially 180° with respect to that of said first signal; means for inverting said fourth signal to obtain a second signal whose phase is shifted substantially 90° with respect to that of said first signal; switching means having first, second, third, and fourth signal inputs and a signal output, said switching means being adapted to respectively couple said first, second, third and fourth signal inputs to said signal output when in first, second, third and fourth positions; means respectively applying said first, second, third and fourth signals to said first, second, third and fourth signal inputs of said switching means; and means for causing said switching means to successively switch among said first, second, third and fourth positions in a predetermined sequence and at said frequency $f_\alpha$ to thereby provide said reference signal at said signal output of said switching means.

7. An apparatus as recited in claim 4, further comprising fifth means operable in synchronism with said third means for successively storing said positive and said negative values of said conductance component and of said susceptance component, and sixth means for taking the absolute difference of said stored positive values and said stored negative values of said conductance component and of said susceptance component to obtain first and second output signals proportional to said conductivity and to said dielectric coefficient.

8. An apparatus as recited in claim 1, further comprising fifth means responsive to said output signal from said third means for providing a first output signal proportional to said conductivity and a second output signal proportional to said dielectric coefficient.

9. An apparatus as recited in claim 1, wherein said fourth means includes a double-balanced mixer.

10. An apparatus for measuring the electrical impedance of a material, said apparatus comprising:
(a) first means for providing a test signal having a predetermined frequency $f_0$;
(b) second means for providing a reference signal whose frequency is identical to that of said test signal, said second means being adapted to successively shift the phase of said reference signal at a frequency $f_\alpha$, where $f_0$ is much greater than $f_\alpha$, so that said reference signal is substantially in-phase, 90° out-of-phase, 180° out-of-phase, and 270° out-of-phase with said test signal;
(c) an electrode adapted to be located in the vicinity of said material;
(d) a bridge circuit adapted to be located in proximity to said electrode, said bridge circuit having first and second inputs and an output;
(e) third means interconnecting said electrode with said second input of said bridge circuit;
(f) fourth means for coupling said test signal to said first input of said bridge circuit, whereby said bridge circuit provides a bridge output signal on its output whose frequency is identical to that of said test signal and whose phase, relative to that of said test signal, and whose amplitude are related to the electrical admittance of said material in the vicinity of said electrode;
(g) a mixer adapted to be located in proximity to said electrode, said mixer having first and second inputs and an output;
(h) fifth means for coupling said bridge output signal to said second input of said mixer;
(i) sixth means for coupling said reference signal to said first input of said mixer, whereby said mixer provides a time-multiplexed mixer output signal on its output having successive first, second, third and fourth DC levels which are respectively proportional to a positive conductance component, to a positive susceptance component, to a negative conductance component, and to a negative suceptance component, of said bridge output signal.

11. An apparatus as recited in claim 10, further comprising means for storing said first, second, third and fourth DC levels; means for taking the absolute difference between said stored first and third DC levels to provide a first output signal proportional to the conductivity of said material; and, means for taking the absolute difference between said stored second and fourth DC levels to provide a second output signal proportional to the dielectric coefficient of said material.

12. An apparatus as recited in claim 10, further comprising temperature compensation means for varying said first, second, third and fourth DC levels of said mixer output signal by an amount sufficient to compensate said mixer output signal for variation in temperature of said material.

13. An apparatus as recited in either of claims 10 or 12, further comprising bulk density compensation means for varying said first, second, third and fourth DC levels of said mixer output signal by an amount sufficient to compensate said mixer output signal for variation in bulk density of said material.

14. An apparatus as recited in claim 10, wherein said fourth and said sixth means respectively include first and second cables having substantially identical lengths and substantially identical characteristic impedances, the first end of said cable being coupled to said first means and the second end of said cable being coupled to said first input of said bridge circuit, and the first end of said second cable being coupled to said signal output of said switching means and a second end of said second cable being coupled to said first input of said mixer.

15. An apparatus as recited in claim 14, further comprising seventh means for coupling said first input and said output of said mixer to said second end of said second cable, whereby both said mixer output signal and said reference signal are carried by said second cable.

16. An apparatus as recited in claim 15, wherein said seventh means includes a first filter circuit interconnected between said second end of second cable and said first input of said bridge circuit for passing only said reference signal therebetween, and a second filter circuit interconnected between said output of said mixer and said second end of said second cable for passing only said mixer output signal therebetween.

17. An apparatus as recited in claim 15, further comprising eighth means interconnected with said first end of said second cable for separating said mixer output signal from said reference signal.

18. An apparatus as recited in claim 14, wherein said bridge circuit includes a first resistance; a first transistor having a base, an emitter and a collector, said first resistance and said emitter of said first transistor being connected in series circuit; a second resistance; a second transistor having a base, an emitter and a collector, said second resistance being connected with said emitter of said second transistor in series circuit; an adjustable impedance connected to the common junction of said first resistance and said emitter of said first transistor; means coupling the common junction of said second resistance and said emitter and said emitter of said second transistor to said second input of said bridge circuit; an adjustable resistance interconnecting said first and said second resistances; a transformer having a primary winding split into first and second, substantially symmetrical portions connected in series opposition, said transformer also having a secondary winding; means coupling said collector of said first transistor to said first portion of said primary winding of said transformer; means coupling said collector of said second transistor to said second porition of said primary winding of said transformer; means coupling said secondary winding of said transformer to said bridge output; and, means coupling the bases of said first and said second transistors in common to said first input of said bridge circuit.

19. An apparatus as recited in claim 10, wherein said bridge circuit includes: an adjustable impedance; first and second circuit branches of identical types; means for interconnecting said adjustable impedance with said first circuit branch; means for interconnecting said second input of said bridge circuit with said second circuit branch; isolation circuit means for interconnecting said first input of said bridge circuit with said first and second circuit branches, said isolation circuit means presenting a relatively high impedance to said first input of said bridge circuit and a relatively low impedance to said first and second circuit branches, whereby said first and second circuit branches carry currents respectively proportional to the admittance of said adjustable impedance and to the admittance of said material; and, means subtractively combining the currents in said first and said second circuit branches and interconnected with said bridge output to provide said bridge output signal.

20. An apparatus as recited in claim 19, wherein said isolation circuit means comprises a pair of transistors each of said transistors having a base, an emitter, and a collector, the bases of said transistors being connected in common to said first input of said bridge circuit, the emitter and collector of one of said transistors being connected in said first circuit branch with the emitter of said one of said transistors being connected to said adjustable impedance, and the emitter and collector of the other of said transistors being connected in said second circuit branch with the emitter of said other of said transistors being connected to said second input of said bridge circuit.

21. An apparatus as recited in claim 10, further comprising a source of an AC signal having a frequency $f_0$, wherein said first means comprises a first phase shift circuit for shifting the phase of said AC signal in a first direction by substantially 45° to obtain said test signal; and, wherein said second means includes: a first phase shift circuit for shifting the phase of said AC signal by substantially 45° in said first direction to obtain a first signal; a second phase shift circuit for shifting the phase of said AC signal by 45° in a second, opposite direction to obtain a second signal; means for inverting said first and said second signals to obtain respective third and fourth signals; switching means having first, second, third and fourth signal inputs and a signal output; means for coupling said first, second, third and fourth signals respectively to said first, second, third and fourth signal inputs of said switching means; said switching means being adapted to successively couple said first, second, third and fourth signal inputs to its signal output in a predetermined sequence and said frequency $f_\alpha$ to develop said reference signal at said signal output of said switching means.

22. An apparatus as recited in claim 10, wherein said mixer comprises a double-balanced mixer.

23. An apparatus as recited in claim 10, wherein $f_0 \simeq 1000 f_\alpha$.

* * * * *